United States Patent
Brigance (12)

(10) Patent No.: US 6,432,878 B1
(45) Date of Patent: Aug. 13, 2002

(54) ADJUVANT COMPOSITION

(75) Inventor: Mickey R. Brigance, Germantown, TN (US)

(73) Assignee: Cognis Corporation, Gulph Mills, PA (US)

( * ) Notice: Subject to any disclaimer, the term of this patent is extended or adjusted under 35 U.S.C. 154(b) by 0 days.

(21) Appl. No.: 09/448,245

(22) Filed: Nov. 24, 1999

Related U.S. Application Data

(60) Provisional application No. 60/116,085, filed on Jan. 15, 1999, provisional application No. 60/117,559, filed on Jan. 28, 1999, and provisional application No. 60/131,662, filed on Apr. 29, 1999.

(51) Int. Cl.[7] ..................... A01N 25/30; A01N 25/32
(52) U.S. Cl. ................. 504/206; 504/362; 514/772; 514/784; 514/975; 516/203; 516/204
(58) Field of Search ................. 504/206, 362, 504/365; 514/772, 784, 975; 516/203, 204

(56) References Cited

U.S. PATENT DOCUMENTS

| | | | | |
|---|---|---|---|---|
| 3,853,530 A | | 12/1974 | Franz | 71/76 |
| 4,478,650 A | | 10/1984 | Zado | 148/23 |
| 5,206,021 A | * | 4/1993 | Dookhith et al. | 424/405 |
| 5,389,598 A | | 2/1995 | Berk et al. | 504/206 |
| 5,703,015 A | | 12/1997 | Berger et al. | 504/206 |
| 5,747,416 A | * | 5/1998 | McArdle | 504/115 |
| 5,863,863 A | | 1/1999 | Hasebe et al. | 504/116 |
| 6,180,566 B1 | * | 1/2001 | Nielsen et al. | 504/206 |

FOREIGN PATENT DOCUMENTS

| | | |
|---|---|---|
| EP | 0472310 A1 | 2/1992 |
| EP | 0 577 914 A1 | 1/1994 |
| EP | 0 566 048 B1 | 6/1995 |
| GB | 1081294 | 12/1962 |
| WO | WO 95/16352 | 6/1995 |
| WO | WO 95/17817 | 7/1995 |

OTHER PUBLICATIONS

D.L. Shaner, "Effects of Glyphosate on Transpiration", Weed Science, Journal of The Weed Science Society of America, vol. 26, No. 5, Sep., 1978, pp. 513–516.

Monsanto Material Safety Data Sheet for Roundup® Herbicide, C&C Press, Nov. 1994.

Monsanto Material Safety Data Sheet for Roundup® Super Concentrate Grass & Weed Kill, Prepared Oct. 1, 1989.

D.J. Turner, "The Effect Of Additives On The Control Of Agropyron Repens With Glyphosate", Conference on Grass Weeds in Cereals in the United Kingdom, University of Reading, Berkshire, England, Jan. 6–7, 1981, pp. 167–175.

D.J. Turner, et al., "Complexing Agents As Herbicide Additives", Weed Research, 1978, vol. 18, pp. 199–207.

* cited by examiner

*Primary Examiner*—S. Mark Clardy
(74) *Attorney, Agent, or Firm*—John E. Drach

(57) ABSTRACT

An adjuvant composition for pesticide formulations which exhibits reduced eye irritancy is comprised of a polyoxyalkylene aliphatic amine containing at least about 2 moles of an alkylene oxide group and an eye irritation reducing compound which simultaneously reduces the eye irritation caused by the polyoxyalkylene aliphatic amine and which complexes with metal ions such as calcium and iron which may be present in an aqueous solution of the adjuvant and a pesticide or a plant growth regulator. The eye irritation reducing compound is a carboxylic add that is capable of complexing with or forming chelates with metal ions in aqueous solution while simultaneously reducing the eye irritation caused by the polyoxyalkylene aliphatic amine. The adjuvant also contains a mixture of polyhydric alcohols and, optionally, a defoamer. The adjuvant is particularly in N-phosphonomethylglycine (glyphosate) herbicidal formulations.

22 Claims, No Drawings

ADJUVANT COMPOSITION

CROSS-REFERENCE TO RELATED APPLICATIONS

This application claims the benefit of copending provisional application Ser. No. 60/116,085, filed on Jan. 15, 1999; provisional application Ser. No. 60/117,559, filed on Jan. 28, 1999; and provisional application Ser. No. 60/131,662, filed on Apr. 29, 1999; the entire contents of each of which are incorporated herein by reference.

STATEMENT REGARDING FEDERALLY SPONSORED RESEARCH OR DEVELOPMENT

Not Applicable.

BACKGROUND OF THE INVENTION

Insecticides, insect repellents, fungicides, bactericides, bacteriostats, herbicides, and plant growth regulators are normally formulated into various products for use on crops, for insect control, weed control and the like. Alternatively, the products may be formulated as liquids or powders or granules. Solvents, emulsifiers, dispersing agents and wetting agents are normally incorporated into such compositions to ensure the preparation of a uniform pesticide formulation.

These formulation components are also selected to ensure that the pesticide composition will disperse or emulsify evenly in a tank mix at the point of application. They also have a third purpose that is to ensure optimum delivery of the tank mix preparation to the targeted pest or substrate. Sometimes the surfactants incorporated in pesticide formulations are not sufficient to fully ensure stable tank mixes when such tank mixes contain multiple components. Similarly, it may be necessary to add adjuvants to the tank mix for full stability. Chemically, surfactants are the most important and widely used adjuvants. Surfactants may affect many properties of the formulation such as solubility, volatility, specific gravity, corrosiveness, efficacy, and freezing and flash points. It is widely known that adding surfactant-based adjuvants to the tank mix will realize the desired stabilization. Adjuvants also potentiate pesticidal activity of many pesticides and there are many adjuvant formulations that have been developed for this purpose. Surfactants are nearly always components of these adjuvants ranging from minor components to the sole component.

One class of adjuvants that has found success in, for example, N-phosphonomethylglycine (glyphosate) formulations containing polyoxyalkylene aliphatic amines such as, for example, ethoxylated tallowamine. While polyoxyalkylene aliphatic amine-based adjuvants have excellent surfactant properties that often enhance the efficacy of aphytotoxicants such as glyphosate, they unfortunately are eye irritants and must be used with a high degree of caution.

Reducing or eliminating the eye irritancy of the polyoxyalkylene aliphatic amine-based adjuvants used with pesticides, without reducing the efficacy of the pesticidal compositions containing the surfactants, is a highly desirable end. The protection of the applicator and personnel preparing the surfactant and pesticidal compositions from eye damage is of paramount importance. Reducing the eye irritancy of the adjuvants and pesticidal compositions containing the adjuvant, increases the use that can be made of such products while lessening the possibility of injury to personnel handling and using them.

BRIEF SUMMARY OF THE INVENTION

The present invention is directed to an adjuvant composition for pesticide formulations which exhibits reduced eye irritancy. The adjuvant composition according to the invention is comprised of a polyoxyalkylene aliphatic amine containing at least about 2 moles of an alkylene oxide group and an eye irritation reducing compound which simultaneously reduces the eye irritation caused by the polyoxyalkylene aliphatic amine and which complexes with metal ions such as calcium and iron which may be present in an aqueous solution of the adjuvant and a pesticide or a plant growth regulator. The eye irritation reducing compound is a carboxylic add that is capable of complexing with or forming chelates with metal ions in aqueous solution while simultaneously reducing the eye irritation caused by the polyoxyalkylene aliphatic amine. The adjuvants according to the invention also contain a mixture of polyhydric alcohols and, optionally, a defoamer. The mixture of polyhydric alcohols is comprised of a trihydric alcohol, such as glycerol and one or more diols, such as ethylene glycol and propylene glycol. The adjuvant according to the invention is particularly useful in N-phosphonomethylglycine (glyphosate) herbicidal formulations. The invention is also directed to a method of killing or controlling weeds which comprises in contacting the weeds with a herbicidally effective amount of the composition according to the invention.

BRIEF DESCRIPTION OF THE SEVERAL VIEWS OF THE DRAWING

Not Applicable

DETAILED DESCRIPTION OF THE INVENTION

The term "pesticide" as used herein includes chemicals and microbial agents used as active ingredients of products for control of crop and lawn pests and diseases, animal ectoparasites, and other pests in public health. The term also includes plant growth regulators, pest repellants, synergists, herbicide safeners (which reduce the phytotoxicity of herbicides to crop plants) and preservatives.

The adjuvant composition of the present invention comprises a polyoxyalkylene aliphatic amine having at least about 2 moles of an alkylene group, the adjuvant composition having an eye irritancy lower than the eye irritancy of the polyoxyalkylene aliphatic amine. The polyoxyalkylene aliphatic amines according to the invention are compounds of the formula I

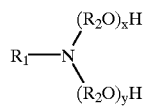

wherein $R_1$ is alkyl or alkenyl group having from 6 to 22 carbon atoms, $R_2$ is an alvlene group having from 2 to 4 carbon atoms, x and y are numbers such that x+y has an average value of from about 2 to about 50. The polyoxyalkylene aliphatic amines are present in the adjuvant in an amount sufficient to increase the efficacy of the pesticide or plant growth regulator with which it is formulated. Such an amount of the polyoxyalkylene aliphatic amines normally causes eye irritation to users of formulations containing a pesticide or plant growth regulator, especially when such formulations are applied by spraying. Preferred polyoxyalkylene aliphatic amines are ethoxylated tallow amines having a degree of ethoxylation of about 20. In reference to compounds having the formula I, such amines are those wherein $R_1$ is a mixture of saturated or unsaturated carbon chains having from about 8 to about 22 carbon atoms, $R_2$ is an ethylene group and x+y has an average value of about 20. The typical amount of polyoxyalkylene aliphatic amine in the adjuvant according to the invention can range from about 5% to about 85% by weight with the preferred amount typically ranging from about 65% to about 75% by weight.

The eye irritation reducing component of the adjuvant of the present invention is a carboxylic which is capable of forming a complex with metal ions in aqueous solution thereby reducing or eliminating the inactivating effect of metal ions on the activity of the pesticide in the formulated product. Such a carboxylic also interacts with the polyoxyalkylene aliphatic amine thereby reducing the eye irritation of the adjuvant and of any pesticide formulation containing the adjuvant.

The carboxylic adds according to the invention also function as chelating agents. It is well known that chelating agents are compounds having donor atoms that can combine by coordinate bonding with a metal ion to form a cyclic structure known as a chelating complex. The donor atoms are present in separate functional groups within the same molecule. Thus, the carboxylic acids according to the invention are those having one or more carboxyl groups and one or more other functional groups capable of interacting with polyvalent metal ions in aqueous solution such that a stable metal chelate is formed. For example, hydroxycarboxylic adds chelate through the oxygen donor atoms located in the carboxyl group and the alcohol group. Other such a carboxylic adds include, but are not limited to, aminocarboxylic acids such as ethylenediaminetetraacetic acid and its salts. N-phosphonomethylglydne (glyphosate) is an example of a herbicide that is partially or completely inactivated in aqueous solution by the presence of metal ions, particularly polyvalent metal ions such as $Ca^{+2}$ and $Fe^{+3}$.

The preferred carboxylic adds are hydroxycarboxylic acids that contain one or more carboxyl groups and one or more hydroxyl groups. Such acids that are particularly useful in the practice of the present invention include, but are not limited to, citric acid, glycolic add, gluconic add, alpha-hydroxybutyric add, malic add, saccharic acid, mandelic add, tartaric add, glyceric acid. Citric add is especially preferred because it is non-toxic and can be used at relatively low concentrations. Another advantage to the use of citric add is its ability to increase the phytotoxicity of the herbicide glyphosate because citric acid readily complexes with metals such as calcium and iron, metals which are known to inactivate glyphosate. The amount of such carboxylic acids that can be present in the compositions according to the invention is an eye irritation-reducing amount which is any amount required to reduce the eye irritation of a pesticidal formulation containing the adjuvant according to the invention to an acceptable level. Such an amount will be readily determinable by those skilled in the art and will typically vary from about 0.05% to about 5% by weight of the adjuvant.

The adjuvants according to the invention also contain a mixture of polyhydric alcohols and, optionally, a defoamer. A polyhydric alcohol or polyol is a compound having at least 2 alcohol functionalities. The mixture of polyhydric alcohols is preferably comprised of at least one trihydric alcohol, preferably glycerol and at least one glycol, preferably ethylene glycol, propylene glycol or a combination thereof. While the mixture of polyhydric alcohols can contain any combination of polyols in any relative amount, it is preferably comprised of a combination of glycerol, ethylene glycol and propylene glycol present in an amount of from about 10% to about 25% by weight of the adjuvant. The relative amounts of the various polyhydric alcohols within the mixture will vary according to the nature of the pesticide and the end use of the pesticidal formulation and will typically be ascertainable to those skilled in the art.

The optimum amount of each component in the adjuvant depends on variables such as the identity of the eye irritation reducing compound, the identity of the pesticide, the type of application of the pesticide composition, storage and transportation of the surfactant and pesticide compositions, the conditions of use of the pesticidal compositions, etc. and is readily determinable by those skilled in the art. The adjuvant of the present invention can contain optional components to improve the water solubility of the surfactant composition and suppress gel formation. The need for such components will depend upon several factors, especially the identity of the surfactants comprising the composition.

When used as an adjuvant with glyphosate, the adjuvant according to the invention is typically used at the level of from about 120 grams to about 180 grams of adjuvant per liter of an aqueous glyphosate solution containing about 480 grams of the isopropylamine salt of phosphonomethyl glycine. This is equivalent to from about 0.2% to about 0.40% by weight of a carboxylic acid having the ability to complex a metal ion.

The adjuvants according to the invention can be combined with a pesticidally effective amount of any type of pesticide to form a pesticidal composition. Examples of pesticides with which the adjuvants according to the invention can be formulated include, but are not limited to, glyphosate and acifluorfen(5(2-chloro-4(trifluoromethyl)phenoxy)-2-nitrobenzoic acid), chloramben(3-amino-2,5-dichlorobenzoic acid), 2,4-D ((2,4-dichlorophenoxy)acetic acid), endothal(7-oxabicydo(2.2.1)heptane-2,3-dicarboxylic acid), mecoprop(2-(2-methyl4chlorophenoxy)propionic acid), picloram(4-amino-3,5,6-trichloropyridine-2-carboxylic acid), 2,4,5-T((2,4,5-trichlorophenoxy)acetic add), benzac(2,3,6-trichlorobenzoic acid), dicamba(3,6-dichlor-o-anisic acid), MCPA(4-chloro-o-tolyloxyacetic acid), dalapon (2,2-dichloropropionic acid), dichlorprop(2-(2,4-dichlorophenoxy)propionic acid), MCPB(4-(4-chloro-o-tolyloxy)butyric acid), bialaphos(L-2-amino-4-((hydroxy)(methyl)phosphinoyl)butyryl-L-alanyl-L-alanine), glufosinate((3-amino-3-carboxypropyl)methylphosphinate), imazethapyr(2-[4,5-dihydro4-methyl4-(1 -methylethyl)-5- oxo-1-H-imidazol-2-yl]-5-ethyl-3-pyridinecarboxylic acid), imazaquin(2-[4,5-dihydro-4-methyl4(1-methylethyl)-5-oxo-1H-imidazol-2-yl]-3-quinolinecarboxylic acid), mixtures thereof and the like. Preferred results, however, are obtained with the herbicide glyphosate whose activity is derived from N-phosphonomethylglycine. Glyphosate is normally formulated from water soluble salts thereof. The use of glyphosate and its derivatives as herbicides is disclosed in U.S. Pat. No. 3,853,530, the entire contents of which is incorporated herein by reference. The adjuvants of the present invention are especially useful in the preparation of pesticidal compositions designed to be delivered by spraying, particularly sprayable herbicidal compositions. When combined with a pesticide, the adjuvants according to the invention can be made into a concentrate which can subsequently be diluted with water to form an aqueous pesticidal composition ready for use by spraying.

Since glyphosate in acid form has limited water solubility (about 1.2%) the water soluble salts of glyphosate are normally used for most applications. Among the water soluble salts of glyphosate are the trimethylsulfonium salt, the ammonium salt, the isopropylamine salt, and the alkali metal salts, such as sodium and potassium. These compounds due to their solubility in water are the agriculturally acceptable glyphosate-containing compounds generally used in commerce. The relative amounts of herbicide, water and surfactant in the aqueous herbicidal compositions of this invention will vary depending upon many factors including but not limited to the identity and properties of the herbicide, method of application, locus to which the herbicide is applied, etc. The weight ratio of glyphosate expressed as acid equivalent to surfactant composition is normally in the range of 1:1 to 5:1.

Formulations containing a herbicide such as glyphoste and the compositions according to the invention are effective at killing and/or controlling the growth of weeds. The following examples are meant to illustrate but not to limit the invention.

EXAMPLE 1

| Adjuvant Composition | |
|---|---|
| | % Weight |
| TRYMEEN ® 6607 | 68.0 |
| Citric Acid (50% Aqueous Solution) | 4.0 |
| Glycerine | 15.0 |
| AGNIQUE ® DF 6889 Defoamer | 0.1 |
| Ethylene Glycol | 2.0 |
| Propylene Glycol | 10.9 |

TRYMEEN ® 6607 is tallow amine ethoxylated with an average of 20 moles of ethylene oxide, a trademark product of Henkel Corporation, Gulph Mills, PA 19406.
AGNIQUE ® DF 6889 Defoamer is a silicone emulsion, a trademark product of Henkel Corporation, Gulph Mills, PA 19406.

EXAMPLE 2

Toxicology Testing Results

A formulation containing 480 g/L (41% by weight) of the isopropylamine salt of glyphosate and 180 g/L (15.3% by weight) of the adjuvant of Example 1 (Sample A), was compared to commercial glyphosate products under the test protocols recited below. This formulation (Sample A) contained about 0.36% citric add by weight. Both types of ROUNDUP® contain the isopropylamine salt of glyphosate and ethoxylated tallow amine.

TABLE 1

| SAMPLE | PDII | EYE | CLEARANCE | IRRITATION | RAINBOW TROUT LC50 |
|---|---|---|---|---|---|
| A | 0.2 | 9.0 | Day 4 (S) 72 Hrs (E) | None (S) Mild (E) | 35.4 |
| B | 0.7 | 20.0 | 72 Hrs (S) Day 10 (E) | Slight (S) Moderate (E) | 12.9 |
| C | 0.6 | 19.5 | 72 Hrs (S) Day 7 (E) | Slight (S) Moderate (E) | 5.7 |

Sample B is ROUNDUP ®
Sample C is ROUNDUP ® ULTRA
PDII is Primary Dermal Irritation Index score of the Primary Skin Irritation Test conforming to U.S. EPA Health Effects Testing Guidelines, OPPTS 870.2500 (1998) and OECD Guidelines for Testing of Chemicals, Procedure 404; and/or JMAFF 59 NohSan No. 4200, January 28, 1985.
Eye is Primary Eye Irritation Test conforming to U.S. EPA Health Effects Testing Guidelines, OPPTS 870.2500 (1998) and OECD Guidelines for Testing of Chemicals, Procedure 404; and/or JMAFF 59 Noh San No. 4200, January 28, 1985. The number is the Maximum Mean Total Score (MMTS) of this test.
Irritation- describes the level of irritation observed in the skin (S) and eye (E) tests.
Clearance- time required for irritation to clear observed in the skin (S) and eye (E) tests.
Rainbow Trout - Static Acute Toxicity Test with Rainbow Trout, Oncorhynchus mnykiss.
Complies with U.S. EPA FIFRA Testing Guideline 72-1.

EXAMPLE 3

The post-emergence herbicidal effect of the composition of Example 2 (Sample A) was evaluated according to the following protocol:

Weed species: Barnyardgrass (ECHCG), giant foxtail (SETFA), green foxtail (SETVI), large crabgrass (DIGSA), wild oats (AVEFA), johnsongrass (SORHA), quackgrass (AGRRE), ivyleaf momingglory (IPOHE), redroot pigweed (AMARE), velvetleaf (ABUTH), cocklebur (XANST), and common lambsquarters (CHEAL), sowthistle (SONAR), Canada thistle (CIRAR), sicklepod (CASOB) and wild poinsettia (EPHHL).

Plants were germinated in synthetic soil mix (Metro-mix, manufactured by the O. M. Scott Co.) containing micronutrients under greenhouse conditions of natural light supplemented by halide light with an average energy of 165 micromols per square meter per second, daylight temperature of 29.4° C. and a relative humidity of 73.7%. The photoperiod was 16 h day and 8 h night. All plants were top watered prior to treatment and sub-irrigated after treatment.

All formulations of glyphosate were brought into solution using tap water with no additional adjuvants added. The appropriate amount of compound was added to 80 ml of water to equal 800, 600, 400, 200, 100 g ae/ha when applied. Applications were made at the 2–3 leaf (B12-B13) stage with a track sprayer manufactured by Allen Machine Works utilizing a 8002E nozzle at 38 psi and a track speed of 2 mph. Application height was 18 inches above the plant canopy. This was the equivalent to an application volume of 187 L/ha. All treatments were replicated three times per species and randomized before transferring treated plant material to zone 12 or 14 for incubation during the duration of the experiment. Injury and phytotoxicity ratings were visual and taken on each pot at 7 and 14 days after treatment (DAT). The entries in the tables below range from 0% meaning no death to 100% meaning total death for a given application rate. The numbers in parentheses at the top of each table represents the number of trials conducted.

TABLE 2

SAMPLE A (TWO)

| GM/HA | IPOHE | ABUTH | SONAR | CIRAR | CHEAL | XANST | AMARE | CASOB |
|---|---|---|---|---|---|---|---|---|
| 100 | 0 | 0 | 0 | 5.9 | 0 | 6.7 | 23.3 | 0 |
| 200 | 5 | 0.9 | 35 | 11.7 | 83.3 | 33.3 | 66.7 | 36.7 |
| 400 | 35 | 61.7 | 84.2 | 35 | 90 | 60 | 83.3 | 54.2 |
| 600 | 60 | 80.6 | 96.5 | 55 | 98.3 | 76.7 | 86.3 | 85 |
| 800 | 53.3 | 91.4 | 98.4 | 53.4 | 100 | 80 | 93 | 93.4 |

TABLE 3

SAMPLE A (TWO)

| GM/HA | EPHHL | SORHA | AVEFA | ECHCG | DIGSA | SETVI | SETFA | AGRRE |
|---|---|---|---|---|---|---|---|---|
| 100 | 10 | 1.7 | 0 | 0 | 0 | 1.7 | 0 | 1.7 |
| 200 | 53.3 | 23.3 | 0.9 | 0 | 38.3 | 72.5 | 60 | 8.4 |
| 400 | 91 | 96.7 | 40 | 76.7 | 69 | 99.9 | 90 | 64.2 |
| 600 | 91.3 | 99.9 | 72.5 | 80 | 77.4 | 100 | 100 | 96.5 |
| 800 | 97.7 | 100 | 87.4 | 85 | 85.9 | 100 | 100 | 95 |

What is claimed is:

1. A water soluble adjuvant composition comprising: (a) polyoxyalkylene aliphatic amine; (b) a mixture of polyhydric alcohols comprising ethylene glycol; and (c) an effective eye irritation reducing amount of a carboxylic acid having the ability to complex a metal ion.

2. The adjuvant of claim 1 wherein the polyoxyalkylene aliphatic amine is ethoxylated tallow amine having an average degree of ethoxylation of from about 2 to about 50.

3. The adjuvant of claim 1 wherein the average degree of ethoxylation is about 20.

4. The adjuvant of claim 1 wherein the mixture of polyhydric alcohols is comprised of glycerol, ethylene glycol and propylene glycol.

5. The adjuvant of claim 1 wherein the amount of the carboxylic add is from about 0.05% to about 5% by weight.

6. The adjuvant of claim 1 wherein the carboxylic acid is an alpha-hydroxycarboxylic acid.

7. The adjuvant of claim 6 wherein the alpha-hydroxycarboxylic add is citric acid.

8. The adjuvant of claim 6 wherein the amount of citric add in the adjuvant is from about 0.05% to about 5% by weight.

9. An adjuvant composition comprising: (a) an ethoxylated tallowamine having an average degree of ethoxylation of from about 2 to about 50; (b) a mixture comprised of glycerol, ethylene glycol and propylene glycol; (c) an effective eye irritation reducing amount of citric acid.

10. The adjuvant of claim 8 wherein the average degree of ethoxylation is about 20.

11. The adjuvant of claim 8 wherein the mixture is comprised of about 15% by weight of glycerol, about 2% by weight of ethylene glycol and about 10.9% by weight of ethylene glycol.

12. The adjuvant of claim 8 wherein the amount of citric acid is about 2% by weight.

13. A water soluble pesticidal composition comprising (a) polyoxyalkylene aliphatic amine; (b) a mixture of polyhydric alcohols comprising ethylene glycol; (c) an effective eye irritation reducing amount of a carboxylic acid having the ability to complex a metal ion; and (d) a pesticidally effective amount of a pesticide.

14. The pesticidal composition of claim 13 wherein the polyoxyalkylene aliphatic amine is ethoxylated tallow amine having an average degree of ethoxylation of from about 2 to about 50.

15. The pesticidal composition of claim 13 wherein the average degree of ethoxylation is about 20.

16. The pesticidal composition of claim 13 wherein the mixture of polyhydric alcohols is comprised of glycerol, ethylene glycol and propylene glycol.

17. The pesticidal composition of claim 13 wherein the amount of the carboxylic acid is from about 0.05% to about 5% by weight.

18. The pesticidal composition of claim 13 wherein the carboxylic acid is an alpha-hydroxycarboxylic acid.

19. The pesticidal composition of claim 17 wherein the alpha-hydroxycarboxylic add is citric acid.

20. The pesticidal composition of claim 17 wherein the amount of citric acid in the adjuvant is from about 0.05% to about 5% by weight.

21. A method of killing or controlling weeds comprising contacting the weeds with a herbicidally effective amount of the composition of claim 13 wherein the pesticide is a herbicide.

22. A method of killing or controlling weeds comprising contacting the weeds with a herbicidally effective amount of a water soluble composition: (a) an ethoxylated tallowamine having an average degree of ethoxylation of from about 2 to about 50; (b) a mixture comprised of glycerol, ethylene glycol and propylene glycol; (c) an effective eye irritation reducing amount of citric acid; and (d) a herbicidally effective amount of N-phosphonomethylglycine or a salt thereof.

* * * * *